United States Patent
Durham et al.

(10) Patent No.: US 9,206,139 B2
(45) Date of Patent: Dec. 8, 2015

(54) AGGRECANASE INHIBITORS

(71) Applicant: Eli Lilly and Company, Indianapolis, IN (US)

(72) Inventors: Timothy Barrett Durham, Indianapolis, IN (US); Jothirajah Marimuthu, Indianapolis, IN (US); Michael Robert Wiley, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/422,018

(22) PCT Filed: Oct. 18, 2013

(86) PCT No.: PCT/US2013/065591
§ 371 (c)(1),
(2) Date: Feb. 17, 2015

(87) PCT Pub. No.: WO2014/066151
PCT Pub. Date: May 1, 2014

(65) Prior Publication Data
US 2015/0218107 A1    Aug. 6, 2015

Related U.S. Application Data

(60) Provisional application No. 61/718,965, filed on Oct. 26, 2012.

(51) Int. Cl.
C07D 233/78 (2006.01)
C07D 233/76 (2006.01)
A61K 31/417 (2006.01)

(52) U.S. Cl.
CPC ............ *C07D 233/78* (2013.01); *A61K 31/417* (2013.01); *C07D 233/76* (2013.01)

(58) Field of Classification Search
CPC ... C07D 233/76; C07D 233/78; A61K 31/417
See application file for complete search history.

(56) References Cited

FOREIGN PATENT DOCUMENTS

WO    02096426 A1    12/2002

OTHER PUBLICATIONS

Shiozaki et al., "Novel N-substituted 2-phenyl-1-sulfonylamino-cyclopropane carboxylates as selective ADAMTS-5 (Aggrecanase-2) inhibitors," Bioorganic & Medicinal Chemistry Letters, vol. 19, No. 6, Mar. 15, 2009, pp. 1575-1580.
Shiozaki et al., "Discovery of (1S,2R,3R)-2,3-Dimethyl-2-phenyl-1-sulfamidocyclopropanecarboxylates: Novel and Highly Selective Aggrecanase Inhibitors," Journal of Medicinal Chemistry, vol. 54, No. 8, Apr. 28, 2011, pp. 2839-2863.
Bursavich et al., "Synthesis and evaluation of aryl thioxothizaolidinone inhibitors of ADAMTS-5 (Aggrecanase-2)," Bioorganic & Medicinal Chemistry Letters, vol. 17, No. 5, Feb. 14, 2007, pp. 1185-1188.

*Primary Examiner* — Samantha Shterengarts
(74) *Attorney, Agent, or Firm* — James J. Sales

(57) ABSTRACT

The present invention provides compounds having the formula: wherein $R_1$ is selected from methyl, ethyl, propyl, cyclopropyl, and dimethyl, or a pharmaceutically acceptable salt thereof, along with methods and intermediates for their preparation, and uses thereof.

(I)

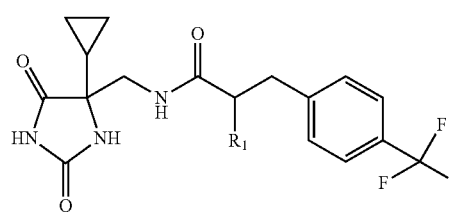

17 Claims, No Drawings

AGGRECANASE INHIBITORS

Connective tissue is a required component of all mammals. It provides rigidity, differentiation, attachments, and, in some cases, elasticity. Connective tissue components include, for example, collagen, elastin, proteoglycans, fibronectin, and laminin. These biochemicals make up (or are components of) structures, such as skin, bone, teeth, tendon, cartilage, basement membrane, blood vessels, cornea, and vitreous humor. Arthritis is a form of joint disorder that involves inflammation of the connective tissue of one or more joints. Regardless of the type of arthritis, the common symptoms for all arthritis disorders include varied levels of pain, swelling, joint stiffness, and sometimes a constant ache around the joint(s).

It is estimated that half of human patients 65 and older, and almost every patient 75 and older, have osteoarthritis. There are many treatments for osteoarthritis (OA), ranging from Tylenol to opiates (for managing OA pain), and at the extreme total joint replacement surgery. Currently there is no approved treatment proven to affect the progression of OA.

Arthritis is much more common in dogs than other domesticated pets. Arthritis is a terrible disease, as it causes the animal pain and restricts mobility. Any dog can be afflicted with arthritis, although older dogs and larger breeds can be more susceptible. Active dogs, like work or hunting dogs, may also be at greater risk because of their increased activity levels.

Biochemical characterization of cartilage in the arthritic joint shows significant loss of two key matrix components, collagen, particularly type II collagen, and aggrecan. Aggrecan degradation is one of the early changes observed in cartilage erosion, particularly in osteoarthritis (OA). Studies have indicated that aggrecan is catabolized by two extracellular matrix proteases identified as aggrecanases. Two aggrecanase proteases, ADAMTS-4 (a disintegrin and metalloprotease with thrombospondin motifs, aggrecanase 1) and ADAMTS-5 (aggrecanase 2), have been identified as particularly effective at catabolizing aggrecan. There is a need to provide a more effective treatment of arthritis, and in particular, treatment of OA.

Degradation, or erosion, of joints occurs in various diseases including rheumitoid arthritis, psoriatic arthritis, osteoarthosis, hypertropic arthritis, and osteoarthritis. Further, acute inflammation of joints may be accompanied by destruction of the cartilage. Examples of diseases involving acute joint inflammation are yersinia arthritis, pyrophosphate arthritis, gout arthritis, and septic arthritis. Also, another factor that may be conducive to destruction or degeneration of cartilage is treatment with cortisone.

The present invention provides compounds that can be useful for treatment of arthritis and in particular, osteoarthritis, as well as inhibiting cartilage erosion. The compounds of the present invention exhibit potency toward ADAMTS 4 and/or ADAMTS 5.

The present invention provides compounds having the formula:

Formula I

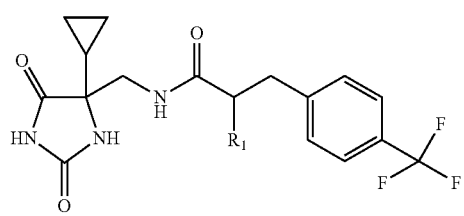

wherein $R_1$ is selected from methyl, ethyl, propyl, dimethyl, and cyclopropyl, or a pharmaceutically acceptable salt thereof. As can be seen in Formula I, the compounds of the inventions have two chiral centers, or one chiral center when $R_1$ is dimethyl:

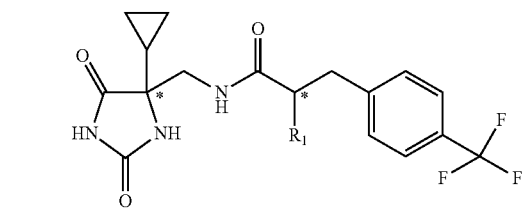

The present invention provides compounds of the formula:

Formula Ia

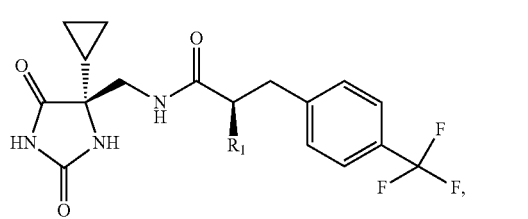

wherein $R_1$ is selected from methyl, ethyl, propyl, and cyclopropyl, or

Formula Im

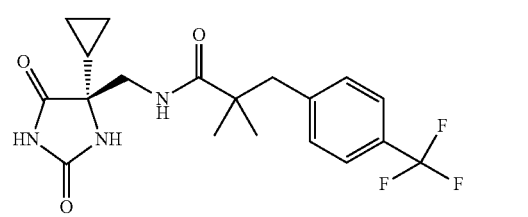

when $R_1$ is dimethyl, and pharmaceutically acceptable salts thereof.

The present invention provides compounds of the formulae:

Formula Ib

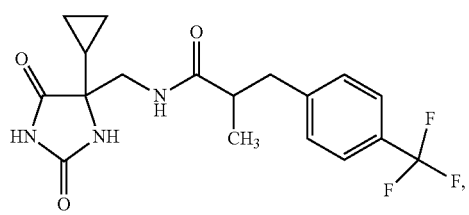

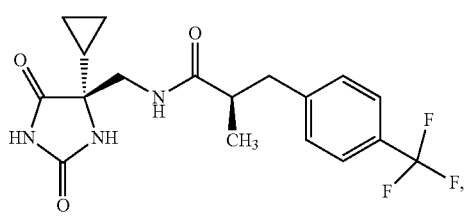
Formula Ic

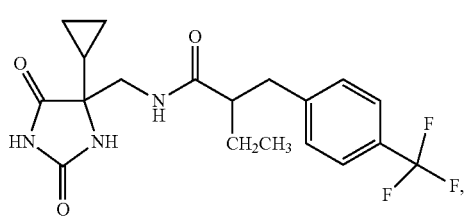
Formula Id

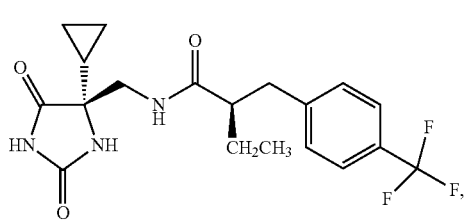
Formula Ie

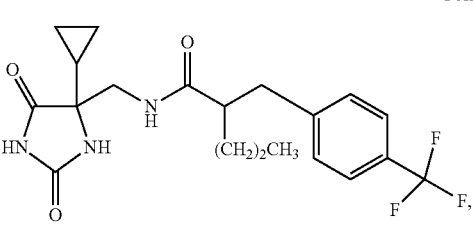
Formula If

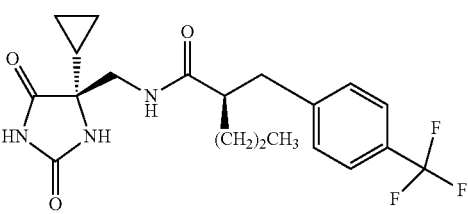
Formula Ig

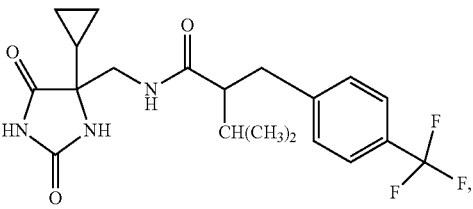
Formula Ih

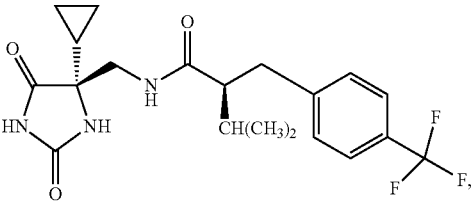
Formula Ii

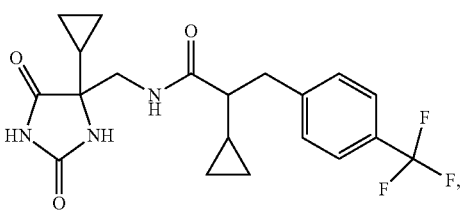
Formula Ij

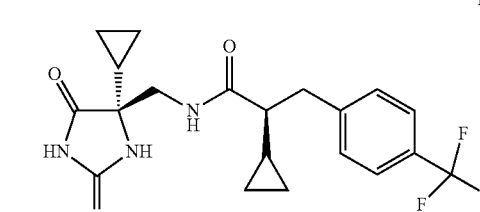
Formula Ik

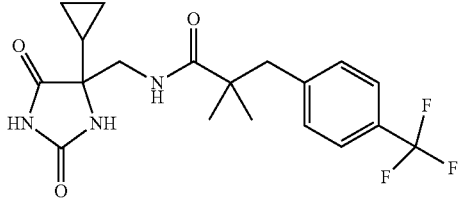
Formula Il

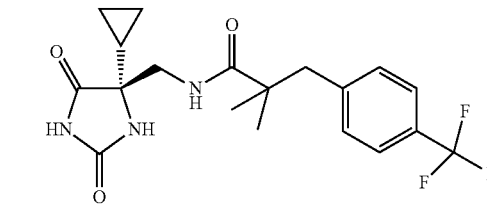
Formula Im and pharmaceutically acceptable salts thereof.

In another aspect, the present invention provides a pharmaceutical composition comprising a compound according to the present invention, or a pharmaceutically acceptable salt thereof, and at least one of a pharmaceutically acceptable carrier, excipient, or diluent.

In another aspect, the present invention provides a method of inhibiting cartilage erosion, such as is seen with osteoarthritis, in a patient in need thereof, which comprises administering an effective amount of a compound according to the present invention, or a pharmaceutically acceptable salt thereof, to said patient.

In another aspect, the present invention provides a method of treating arthritis in a patient in need thereof, which comprises administering an effective amount of a compound according to the present invention, or a pharmaceutically acceptable salt thereof, to said patient.

In another aspect, the present invention provides use of a compound according to the present invention, or a pharmaceutically acceptable salt thereof, for the manufacture of a medicament, and particularly a medicament for treatment of arthritis or inhibition of cartilage erosion.

In another aspect, the present invention provides a compound according to the present invention, or a pharmaceutically acceptable salt thereof, for use in therapy.

In another aspect, the present invention provides a compound according to the present invention, or a pharmaceutically acceptable salt thereof, for use in the treatment of arthritis or inhibition of cartilage erosion.

In another aspect, the present invention provides a compound, method, use, or composition according to the present invention, in combination with one or more other active agents.

As noted above, preferred compounds of the invention exhibit improved binding to aggrecanase, in particular ADAMTS4/5 and inhibit its/their activity. Consequently, these compounds can inhibit the degradation of aggrecan. Inhibiting the degradation of aggrecan in cartilage can be used in the treatment of arthritis, preferably OA, and/or its/their pathological sequela or symptoms.

"Patient" refers to a mammal, and includes, humans, other primates (e.g., monkeys, chimpanzees, etc.), companion animals (e.g., dogs, cats, horses, etc.), farm animals (e.g., goats, sheep, pigs, cattle, etc.), laboratory animals (e.g., mice, rats, etc.), and wild and zoo animals (e.g., wolves, bears, deer, etc.). The term "patient" also refers to mammals that are suffering from adverse pathological effects of cartilage erosion, arthritis, and/or osteoarthritis, particularly humans and/or companion animals such as dogs and cats or domesticated animals such as horses.

"Effective amount" refers to the amount of a compound of the present invention, or a pharmaceutically acceptable salt thereof, sufficient treat arthritis or osteoarthritis, and/or one or more of the sequelae of arthritis or osteoarthritis. For use on or in mammals, ranges for the methods include from 0.01 to 1000 mg/kg and more desirably, 0.1 to 100 mg/kg of the mammal's body weight. The frequency of the administration will also be dependent upon several factors, and can be a single dose administered once a day, once a week, or once a month, for a duration determined by the attending doctor or veterinarian. Additional active agents may be administered with the compounds of the present invention.

"Pharmaceutically acceptable" as used in this application, for example with reference to salts and formulation components such as carriers, refers to those salts and components which are not deleterious to the patient and which are compatible with other ingredients, active agents, salts, or components. Pharmaceutically acceptable includes "veterinarily acceptable", and thus includes both human and non-human mammal applications independently.

"Inhibit" refers to its generally accepted meaning which includes prophylactically treating a patient subject to incurring cartilage erosion, and holding in check and/or treating existing cartilage erosion in a patient. As such, the present method includes both medical therapeutic and/or prophylactic treatment, as appropriate.

As used herein, the term "administering" refers to administering an effective amount of a compound of the present invention to a patient. Administration may occur through various means, including oral administration, parenteral administration such as injection (intramuscular, subcutaneous, intravenous, intraperitoneal) or the like; or topical application with or without transdermal penetration, for example.

Compounds of the present invention inhibit aggrecanase and thus may have advantageous use in treating arthritis and especially preferred for treating OA. As used herein, the term "effective amount" means an amount of compound of the present invention, i.e., Formula I, which is capable of, or effective for, treating or alleviating the symptoms of the various pathological conditions herein described. It will be understood that the amount of the compound actually administered will be determined by a physician considering a patients relative circumstances and conditions, such as age, weight, progression and severity of disease. The compounds of the present invention are preferably formulated as pharmaceutical compositions administered by a variety of routes. Most preferably, such compositions are for oral administration, such as in tablet, capsule, solution, or suspension form.

Thus, another aspect of the present invention is a pharmaceutical composition comprising an effective amount of a compound of the present invention, or a pharmaceutically acceptable salt thereof. Examples of pharmaceutically salts can be found in S. M. Berge, et al., "Pharmaceutical Salts," *J. Phar. Sci.*, 66: 1-19 (1977) and "A Handbook of Pharmaceutical Salts Properties, Selection, and Use", Wermuth, C. G. and Stahl, P. H. (eds.) Verlag Helvtica Chimica Acta, 2002. For example, the compounds of invention can be formulated with pharmaceutically acceptable excipients, diluents, or carriers, and formed into tablets, capsules, suspensions, solutions, powders, and the like. Pharmaceutical compositions and processes for their preparation are known in the art and examples can be found in Remington, "The Science and Practice of Pharmacy" (A. Gennaro, et al. eds. 19$^{th}$ ed. Mack Publishing Co. 1995) which is incorporated by reference herein. Formulations can be administered through various means, including oral administration, parenteral administration such as injection (intramuscular, subcutaneous, intravenous, intraperitoneal) or the like; topical application with or without transdermal penetration. Additional active agents may be included in the formulation containing a compound of the invention.

In addition to pharmaceutically acceptable salts, other salts are included in the present invention. They may serve as intermediates in the purification of compounds or in the preparation of other pharmaceutically-acceptable salts, or are useful for identification, characterization or purification.

The compounds of the present invention may find advantageous use for treating arthritis and the attendant sequelae. As used herein the term arthritis includes, but is not limited to, rheumatoid arthritis (RA), juvenile rheumatoid arthritis, systemic lupus erythematosus (SLE), gout, scleroderma, psoriatic arthritis, ankylosing spondylitis, osteo arthritis (OA), and Reiter's syndrome (reactive arthritis). The compounds of the present invention may find particularly advantageous use in the treatment of osteoarthritis (OA).

When used in combination with another active agent, for example an anti-inflammatory agent or an agent to relieve pain, which can be either a steroidal or non-steroidal agent. The compound of the present invention and the other active agent can be administered concurrently either in a single formulation or in separate formulations. Alternatively, the compound of the present invention and the other agent can be administered sequentially or as needed by the patient.

As used herein, the following terms have the meanings indicated: "n-BuLi" refers to n-butyl lithium; "DCM" refers to dichloromethane; "Dibal-H" refers to diisobutylaluminum hydride; "DMF" refers to N,N-dimethylformamide; "DMSO" refers to dimethylsulfoxide; "EDTA" refers to ethylenediaminetetraacetic acid; "EtOAc" refers to ethyl acetate; "Et$_2$O" refers to diethyl ether; "EtOH" refers to ethanol; "Ex" Refers to Example; "IPA" refers to isopropyl alcohol; "LDA" refers to lithium diisopropylamide; "MeOH" refers to methanol; "Prep" refers to preparation; "t-boc or boc" refers to tert-butoxycarbonyl; TFA refers to trifluoroacetic acid; "THF" refers to tetrahydrofuran; "X" as used herein refers to halides, i.e., I, Br, Cl, or F; "IC$_{50}$" refers to the concentration of an agent that produces 50% of the maximal inhibitory response possible for that agent.

Compounds according to the present invention can be prepared in accordance with reactions as depicted in the following Examples.

PREPARATION 1

(5R)-5-(aminomethyl)-5-cyclopropyl-imidazolidine-2,4-dione hydrochloride

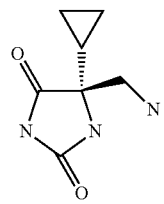
ABS

Step 1: synthesis of tert-butyl N-[2-(methoxy(methyl)amino)-2-oxo-ethyl]carbamate

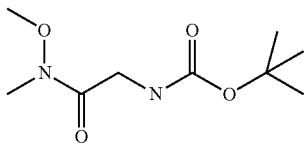

To a solution of Boc-Gly-OH (4250 g, 24.26 mol), N,O-dimethylhydroxylamine-HCl (2839 g, 29.10 mol) and DMAP (297 g, 2.43 mol) in dichloromethane (36 L), is added triethylamine (5.54 L) at 0° C. over a period of 90 min followed by the addition of EDC hydrochloride (5674 g, 29.60 mol). The mixture is stirred at 0° C. for 1 h then warmed to room temp for 24 h. The reaction mixture is cooled to 0° C. and quenched with 1.0M HCl to pH 3 to 4, stirred at room temp for 20 min, then allowed to stand and separate. The organic phase is washed successively with 1.0M HCl (15 L), water (15.0 L) and brine (8.0 L), dried over Na₂SO₄ and filtered. The filtrate is concentrated under reduced pressure to provide the title compound (4985 g; 94% yield) as a white solid.

Step 2: Synthesis of tert-butyl N-(2-cyclopropyl-2-oxo-ethyl)carbamate

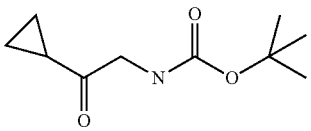

To a solution of tert-butyl N-[2-(methoxy(methyl)amino)-2-oxo-ethyl]carbamate (2,455.3 g, 11.25 mol) in THF (9.0 L) is added 2.0M isopropylmagnesium chloride in THF (5.34 L, 10.69 mol) at −30° C. via an addition funnel over a period of 60 min such that the internal temperature does not exceed 0° C. The mixture is then warmed slowly to 10° C. and 0.5M cyclopropylmagnesium bromide in THF (27.0 L, 13.50 mol) is added via an addition funnel over a period of 1 h. The mixture is stirred at room temp 24 h. The mixture is cooled to 0° C. and quenched with 1.0M HCl to pH 5-6, then warmed to room temp and extracted with EtOAc (12 L and 10 L). The combined organic phase is washed successively with water (10 L) and brine (8 L), dried over Na₂SO₄, and filtered. The filtrate is evaporated under reduced pressure to afford 2.24 kg (100% yield) of the title compound as a light yellow oil which is used directly for the next step.

Step 3: Synthesis of tert-butyl N-[(4-cyclopropyl-2,5-dioxo-imidazolidin-4-yl)methyl]carbamate

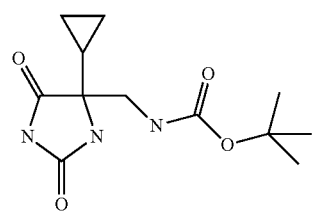 [SMILES: CC(C)(C)OC(=O)NCC1(C2CC2)NC(=O)NC1=O]

A mixture of compound tert-butyl N-(2-cyclopropyl-2-oxo-ethyl)carbamate (4204 g, ~21.10 mol), KCN (1786 g, 27.43 mol) and (NH₄)₂CO₃ (4866 g, 50.64 mol) in methanol (16.0 L) and DI water (19.5 L) is stirred at 65° C. for 72 h. The mixture is concentrated under reduced pressure to remove most of methanol, and then extracted with EtOAc (5×20 L). The organic phase is washed with brine (8.0 L), dried (Na₂SO₄) and filtered. The combined filtrate is split in two equal portions. Each portion is concentrated to a volume of 15 L and allowed to stand overnight at room temp. The precipitates are filtered and washed with EtOAc (3×1.0 L). The resulting white solid is combined and dried under vacuum at 45° C. for 3 days to afford the title compound (3605 g, 64.3% yield).

Step 4: Isolation of tert-butyl N-[[(4R)-4-cyclopropyl-2,5-dioxo-imidazolidin-4-yl]methyl]carbamate

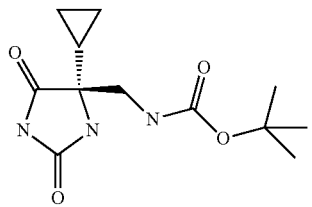
ABS

The enantiomers of tert-butyl N-[(4-cyclopropyl-2,5-dioxo-imidazolidin-4-yl)methyl]carbamate can be separated using a chiral column. Column: 11×33 cm Chiralpak AD®, 20 mu; Flow Rate/detection: 800 mL/min/230 nm; Mobile phase: Methanol.

Step 5: Synthesis of (5R)-5-(aminomethyl)-5-cyclopropyl-imidazolidine-2,4-dione hydrochloride

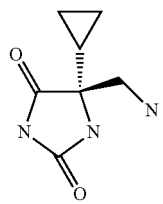
ABS tert-butyl N-[[(4R)-4-cyclopropyl-2,5-dioxo-imidazolidin-4-yl]methyl]carbamate (310 g, 1151 mmol) is dissolved in MeOH (3.1 L) at 6° C. 4M HCl in dioxane (310 mL) is added and the mixture warmed to 25° C. After stirring for 22 h, a second portion of 4M HCl in dioxane (110 mL) is added and stiffing continued for an additional 16 h. The reaction is then allowed to sit with no agitation for 2 days. The mixture is then diluted with toluene (6 L). The title compound is collected by filtration of the mixture as a white solid (180 g).

EXAMPLE 1

(2R)—N-[[(4R)-4-cyclopropyl-2,5-dioxo-imidazolidin-4-yl]methyl]-2-methyl-3-[4-(trifluoromethyl)phenyl]propanamide Formula Ic

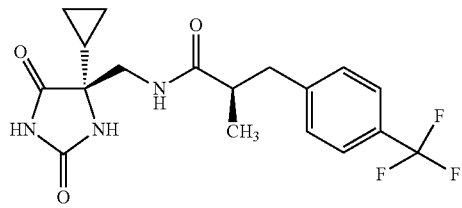

The synthesis as essentially described in Example 2 may be used to make the above compound, by using propanoyl chloride instead of butanoyl chloride.

EXAMPLE 2

(2R)—N-[[(4R)-4-cyclopropyl-2,5-dioxo-imidazolidin-4-yl]methyl]-2-[[4-(trifluoromethyl)phenyl]methyl]butanamide Formula Ie

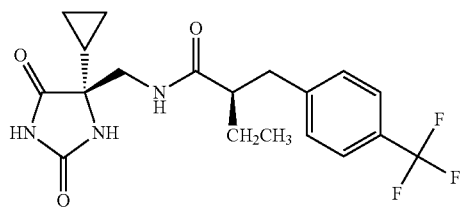

Step 1: Synthesis of (4S)-4-benzyl-3-butanoyl-oxazolidin-2-one

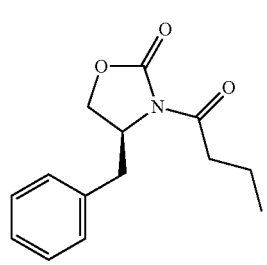

To a 3-necked RBF (round bottomed flask) is added dichloromethane (2.4 L), (S)-4-benzyl-2-oxazolidinone (200 g, 1.13 moles) and N,N-Dimethyl-4-pyridinamine, (13.6 g; 111.32 mmoles). The flask is cooled in an ice water bath and triethylamine (472 mL; 3.39 moles) is added dropwise at 0° C. To the resulting solution is then added dropwise butanoyl chloride (152.2 mL; 1.46 moles) over 3 h, while keeping the temperature below 5° C. The reaction is then filtered and the filtrate is washed with 1M HCl (aq.) (500 ml×1) and saturated NaHCO$_3$ (500 ml×1). The organic phase is dried over Na$_2$SO$_4$, filtered, and concentrated to afford the title compound (275 g, MS:[M+H]$^+$=248.1 m/z).

Step 2: Synthesis of (4S)-4-benzyl-3-[(2R)-2-[[4-(trifluoromethyl)phenyl]methyl]butanoyl]oxazolidin-2-one

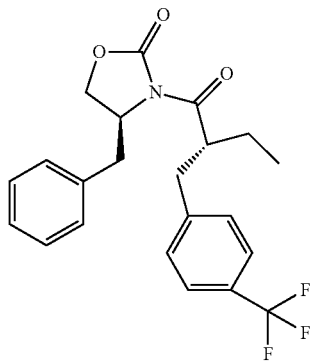 [SMILES: CC[C@H](Cc1ccc(C(F)(F)F)cc1)C(=O)N1C(=O)OC[C@@H]1Cc1ccccc1]

To a 3-necked 5 L RBF is added THF (2 L) and (4S)-4-benzyl-3-butanoyl-oxazolidin-2-one (270 g 1.09 moles) under N$_2$. The resulting solution is cooled to −68° C. in an acetone-dry ice bath. To the cold solution is added sodium bis(trimethylsilyl)amide (1320 mL of 1M THF solution; 1.32 moles) dropwise over 1.5 h while the internal temperature is held between −68 to −60° C. Upon completion of the addition, the reaction is stirred at −68° C. for 30 min. To the cold solution is then added 4-trifluoromethylbenzyl bromide (278 g; 1.16 moles) in THF (1 L) over 30 min at −68° C. After 1.5 h, the reaction is poured into 1 M HCl. The mixture is extracted with ethyl acetate (3 L×1). The extracts are combined and washed with aq. NaHCO$_3$ (2 L×1) and brine (2 L×1). The organic phase is dried over Na$_2$SO$_4$, filtered, and concentrated. The solid is triturated with EtOH (600 mL) at 15° C. Filtration provides the title compound as a solid (270 g, MS:[M+H]$^+$=406 m/z).

Step 3: Synthesis of (2R)-2-[[4-(trifluoromethyl)phenyl]methyl]butanoic acid

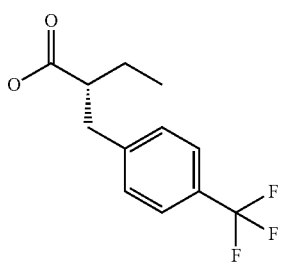

To a 3-necked RBF is added tetrahydrofuran (4.2 L) and water (0.8 L). (4S)-4-benzyl-3-(2-(benzyloxy)-3-(4-(trifluoromethyl)phenyl)propanoyl)oxazolidin-2-one (250 g; 616.65 mmoles) is added and the solution cooled to 0° C. Hydrogen peroxide (4.93 moles; 500.30 mL) is added dropwise over 45 min LiOH (1.08 moles; 45.28 g) in 1.2 L water is added dropwise over 1 h. The resulting mixture is then stirred at 2° C. for 1 h. Sodium Sulfite (2.47 moles; 310.90 g) is dissolved in 2 L of water, and the resulting solution added to the reaction mixture dropwise over 1 h. Upon completion of the addition, the mixture is washed with DCM (2×2 L; 1 L×1). The aqueous phase is then acidified with concentrated HCl (100 ml) to pH=1. The resulting suspension is extracted with EA (2 L×2). The organic extracts are combined, washed with Na$_2$SO$_3$ solution (2 L×1) and brine I (2 L×1), dried over Na$_2$SO$_4$, and filtered to afford the title compound (140 g, MS:[M+H]$^+$=247 m/z) cl Step 4: Synthesis of (2R)—N-[[(4R)-4-cyclopropyl-2,5-dioxo-imidazolidin-4-yl]methyl]-2-[[4-(trifluoromethyl)phenyl]methyl]butanamide (Example 2)

Formula Ie

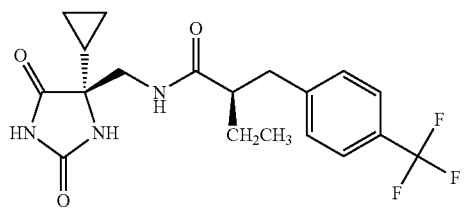

To a 3-necked RBF (2 L) is added dichloromethane (996 mL), dimethylformamide (200 mL), (2R)-2-[[4-(trifluoromethyl)phenyl]methyl]butanoic acid (53 g, 215 mmoles) and 0-(7-azabenzotriazol-1-yl)-N,N,N',N'-tetramethyluronium hexafluorophosphate (215 mmoles; 81.84 g) at ambient temperature under a nitrogen atmosphere. To the mixture is added N,N-dimethyl-ethanamine (1.08 moles; 116.80 mL) in one portion. The mixture is stirred for 30 min. To the resulting solution is added (5R)-5-(aminomethyl)-5-cyclopropyl-imidazolidine-2,4-dione hydrochloride (237 mmoles; 49 g) in one portion. The resulting solution is stirred for 2.5 h. The stirring is then stopped and the mixture is allowed to stand open to the air for 16 h. The reaction mixture is then diluted with EtOAc (200 mL) and washed with 2M HCl (aq.) (200 ml×2), 5% NaHCO$_3$ (aq.) (200 ml×2) and brine (500 mL). The organic phase is dried over Na$_2$SO$_4$, filtered, and concentrated to an oil. The oil is diluted with CH$_2$Cl$_2$ (250 mL) causing a white solid to precipitate out. The solid is collected by filtration and washed with petroleum ether (100 mL×2) to give the title compound (55 g; MS:[M+H]$^+$=398 m/z).

EXAMPLE 3

(2S)-2-cyclopropyl-N-[[(4R)-4-cyclopropyl-2,5-dioxo-imidazolidin-4-yl]methyl]-3-[4-(trifluoromethyl)phenyl]propanamide Formula Ik

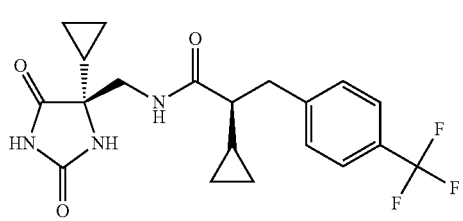

The synthesis as essentially described in Example 2 may be used to make the above compound, by using 2-cyclopropylacetyl chloride instead of butanoyl chloride.

EXAMPLE 4

(2S)—N-[[(4R)-4-cyclopropyl-2,5-dioxo-imidazolidin-4-yl]methyl]-3-methyl-2-[[4-(trifluoromethyl)phenyl]methyl]butanamide Formula Ii

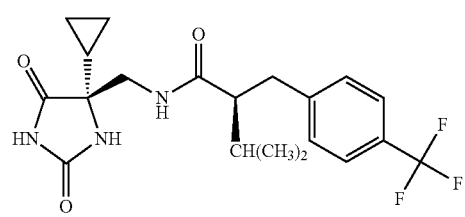

The synthesis as essentially described in Example 2 may be used to make the above compound, by using 3-methylbutanoyl chloride instead of butanoyl chloride.

EXAMPLE 5

N-[[(4R)-4-cyclopropyl-2,5-dioxoimidazolidin-4-yl]methyl]-2,2-dimethyl-3-[4-(trifluoromethyl)phenyl]propanamide Example Im

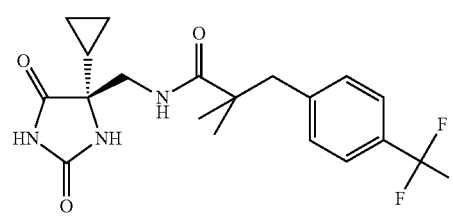

Step 1: Synthesis of (E)-2-methyl-3-[4-(trifluoromethyl)phenyl]prop-2-enoate

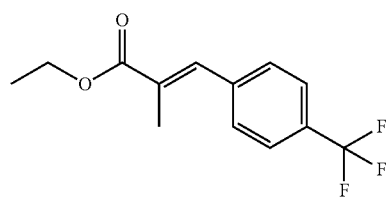 [SMILES: CCOC(=O)/C(C)=C/c1ccc(C(F)(F)F)cc1]

Dissolve ethyl 2-diethoxyphosphorylpropanoate (5.24 g, 22 mmol) and 4-(trifluoromethyl)benzaldehyde (3.48 g, 20 mmol) in dry THF (50 mL) under a nitrogen atmosphere. Cool the resulting solution to 0° C. Carefully add 60% wt NaH (960 mg, 24 mmol). Allow to warm to ambient temperature and stir for 12 h. Concentrate the reaction. Purify the residue using flash chromatography (5% EtOAc/petroleum ether) to give the title compound (4.18 g).

Step 2: Synthesis of ethyl 2-methyl-3-[4-(trifluoromethyl)phenyl]propanoate

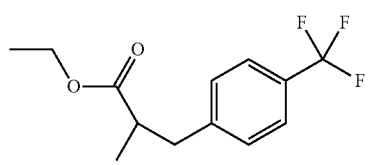 [SMILES: CCOC(=O)C(C)Cc1ccc(C(F)(F)F)cc1]

Dissolve ethyl(E)-2-methyl-3-[4-(trifluoromethyl)phenyl] prop-2-enoate (2.58 g, 10 mmol) in a suspension of 10 wt % Pd—C (258 mg)/MeOH (20 mL) in an RBF under nitrogen, as exposure of Pd—C to oxygen can lead to fire. Carefully purge the flask with hydrogen and stir the resulting mixture under hydrogen (1 Atm) for 16 h. Purge the flask nitrogen and degas the solvent to remove all hydrogen before exposing to air. Filter the suspension through a pad of celite. Concentrate the filtrate to give the title compound (2.39 g).

Step 3: Synthesis of ethyl 2,2-dimethyl-3-[4-(trifluoromethyl)phenyl]propanoate

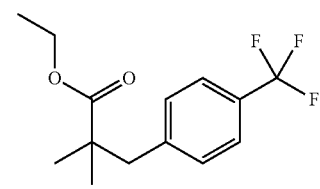 [SMILES: CCOC(=O)C(C)(C)Cc1ccc(C(F)(F)F)cc1]

To a solution of LDA (2.9 mL of 2 M) in THF (30 mL) at −78° C. add ethyl 2-methyl-3-[4-(trifluoromethyl)phenyl]propanoate (1 g, 3.85 mmol). Stir for 10 min, then add methyl iodide (1.48 g, 10.4 mmol) and stir for an additional 15 min Quench the reaction with 10 mL of 1 N HCl and allow to warm to ambient temperature. Extract with EtOAc (50 mL). Wash extract with brine, dry over sodium sulfate, filter, and concentrate. Purify the residue by flash chromatography (5% EtOAc in petroleum ether) to give the title compound (475 mg).

Step 4: Synthesis of 2,2-dimethyl-3-[4-(trifluoromethyl)phenyl]propanoic acid

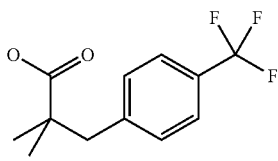 [SMILES: CC(C)(Cc1ccc(C(F)(F)F)cc1)C(=O)O]

Dissolve ethyl 2,2-dimethyl-3-[4-(trifluoromethyl)phenyl]propanoate (400 mg, 1.46 mmol) in MeOH (2 mL) and add aqueous NaOH solution (3 mL of 3 N). Heat to 80° C. and stir for 3 h. Cool to ambient temperature and acidify with 1 N HCl until pH 4. Extract with EtOAc. Combine organic extracts, wash with brine, dry over sodium sulfate, filter, and concentrate to give the title compound (272 mg).

Step 5: Synthesis of N-[[(4R)-4-cyclopropyl-2,5-dioxo-imidazolidin-4-yl]methyl]-2,2-dimethyl-3-[4-(trifluoromethyl)phenyl]propanamide Example 1m

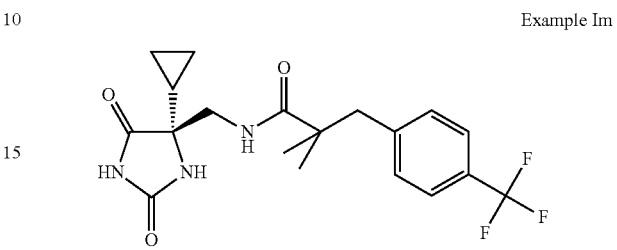

To a solution of amine (205 mg, 1 mmol) in 15 mL of dry acetonitrile add N,N-diidopropylethyl amine (387 mg, 3 mmol). To the resulting solution add 2,2-dimethyl-3-[4-(trifluoromethyl)phenyl]propanoic acid (246 mg, 1 mmol), EDCI (229 mg, 1.2 mmol), and HOAT (163 mg, 1.2 mmol). Stir for 12 h at ambient temperature. Use preparative HPLC to isolate the title compound (282 mg).

| Example | ESMS [M + H] + m/z |
|---------|--------------------|
| 1       | 384.2              |
| 2       | 398.0              |
| 3       | 410.0              |
| 4       | 412.2              |
| 5       | 398.0              |

The following assay protocols and results further demonstrating the utility and efficacy of the compounds and/or methods of the current invention are given for the purpose of illustration and are not meant to be limiting in any way. All ligands, radiolabels, solvents, and reagents employed in the following assays are readily available from commercial sources, or can be readily synthesized by one skilled in the art.

Aggrecanase binding assays are performed to demonstrate that compounds included within the present invention exhibit affinity for aggrecanase. More specifically, the preferred compounds of present invention exhibit improved affinity for aggrecanase as exemplified by their binding affinity in the ADAMTS-4 and ADAMTS-5 AlphaScreen assays.

Matrix metalloproteases (MMPs) are known to be involved in several homeostatic processes including tissue remodeling, sheddase activity and endocytosis. Broad spectrum MMP inhibitors tested in the clinic have been associated with fibroplasia and joint stiffness and related side effects collectively termed as musculoskeletal syndrome (MSS). Therefore, selectivity for aggrecanase over MMPs in general is desired. Similarly, for the ADAMTS family, several members have been associated with critical functions different from the desired aggrecanase inhibition. Compounds of the present invention also exhibit potency (i.e. inhibiting ADAMTS-4 and ADAMTS-5) in plasma and/or increased selectivity for ADAMTS-4 and ADAMTS-5 over MMP-2 and MMP-14.

ADAMTS-4 and ADAMTS-5 AlphaScreen Assay:

The compounds of the present invention can be evaluated by using an aggrecanase ADAMTS-4 and ADAMTS-5 AlphaScreen assay (Miller J. A., et al. *Anal. Biochem.* 2003, 314, 260-265), with the following modifications: Typically 3 or 4 nM ADAMTS-4 or 2.1 nM ADAMTS-5 is incubated with 80 nM 43-mer peptide substrate+/− inhibitors (1% final DMSO concentration) for 3 hours at room temperature in a white non-binding surface 96 well plate (Corning 3990). Inhibitors are serially diluted 3-fold and tested at final starting concentrations of up to approximately 100 μM. The assay is then quenched with a cocktail containing EDTA (62.5 mM), 50 mM Tris(hydroxymethyl)aminomethane (Tris), (pH 7.5), 10 mM calcium chloride, 100 mM sodium chloride, 0.2% Brij® 35 (main component of polyoxyethylene (23) lauryl ether), 0.1% Bovine Serum Albumin (BSA), BC3 monoclonal antibody hybridoma supernatant (1:2000 final dilution), streptavidin conjugated donor beads and anti-mouse IgG conjugated acceptor beads (15 ng/mL final concentration for both beads). The plate is covered with aluminum foil tape and the binding is allowed to incubate overnight. The plate is then read on an AlphaScreen Fusion Alpha reader from Perkin Elmer. Data is analyzed using ActivityBase™ software (IDBS Alameda, Calif.). A similar assay is used with purified dog ADAMTS-4 enzyme. Data from representative compounds of the invention are provided below in Table 1.

TABLE 1

| Ex. No. | ADAMTS-4 IC$_{50}$ (μM) | ADAMTS-5 IC$_{50}$ (μM) | Dog ADAMTS-4 IC$_{50}$ (μM) |
| --- | --- | --- | --- |
| 1 | 0.002 | 0.001 | 0.001 |
| 2 | 0.002 | 0.002 | 0.001 |
| 3 | 0.002 | 0.002 | 0.002 |
| 4 | 0.014 | 0.008 | NA |
| 5 | 0.007 | 0.004 | NA |

Rat and Dog Plasma Shift AlphaScreen Assay

The AlphaScreen Assay is modified to include the testing of inhibitors against ADAMTS-5 in the presence of 50% Lewis rat plasma in order to determine the effects of plasma protein binding on inhibitor potency. The ratio between the IC$_{50}$ of the inhibitor against ADAMTS-5 in 50% Lewis rat plasma versus the IC$_{50}$ of the inhibitor in buffer is calculated and is described as the plasma shift of the inhibitor. The assay is completed in the same manner using 10 nM ADAMTS-5 instead of 2.1 nM. A similar assay is used with dog ADAMTS-4 in the presence of 25% dog plasma. Data from representative compounds of the invention are provided below in Table 2.

TABLE 2

| Ex. No. | Rat Plasma IC$_{50}$ (μM) | Dog Plasma IC$_{50}$ (μM) |
| --- | --- | --- |
| 1 | 0.015 | 0.183 |
| 2 | 0.020 | 0.326 |
| 3 | 0.018 | 0.101 |

TABLE 2-continued

| Ex. No. | Rat Plasma IC$_{50}$ (μM) | Dog Plasma IC$_{50}$ (μM) |
| --- | --- | --- |
| 4 | 0.146 | NA |
| 5 | 0.064 | NA |

In Vitro Fluorescence Assay of MMP-2 Activity

A continuous assay is used in which the substrate is a synthetic peptide containing a fluorescent group (7-methoxy-coumarin, Mca), which is quenched by energy transfer to a 2,4-dinitrophenyl group. The substrate is the peptide Mca-PQGL-(3-[2,4-dinitrophenyl]-L-2,3-diaminopropionyl)-AR-OH. When the peptide is cleaved by MMP a large increase in fluorescence is observed. The source of the enzyme for this assay is full-length, recombinant, human pro-MMP-2 expressed in Chinese Hamster Ovary (CHO) cells that is subsequently activated by an organomercurial compound, 4-aminophenyl mercuric acetate (APMA). APMA is removed through a desalting column (MMP-2 Calbiochem® catalog number PF023). The assay buffer consists of 100 mM Tris-HCl (pH 7.5), 100 mM NaCl, 10 mM CaCl$_2$ and 10 μM human serum albumin Each well of the 96-well plates consists of a 100 μL reaction mixture consisting of assay buffer, MMP (final concentration of 0.2 nM, prepared by diluting in assay buffer), and varied concentrations of inhibitor (prepared by serially diluting a given inhibitor in DMSO in a 96-well polypropylene plate using a 10 point or 11 point dilution scheme). The enzymatic reactions are initiated by adding the substrate to a final concentration of 20 μM. The final DMSO concentration in the assay is 1.0%. The plate is incubated for 2-4 hours at room temperature and substrate cleavage is determined at room temperature with a fluorescence plate reader (excitation filter 320 and emission filter 436) on a LJL Analyst® or a Wallac Envision®.

The data is analyzed by using ActivityBase® software programs vs. 5.3 using a 4 parameter fit model equation 205 from which relative IC$_{50}$'s are generated. Maximum signal is calculated from wells untreated by inhibitor but having enzyme, substrate and 1.0% DMSO. Minimum signal is calculated from wells having buffer only (no enzyme), substrate, and 1.0% DMSO.

In Vitro Fluorescence Assay of Other MMP Activity

Essentially the same procedure is used for the remaining MMP assays as the MMP-2 assay, above, or as known in the art. For example, for MMP-14, the enzyme source is MMP-14 (MT1-MMP) catalytic domain produced by activation of a recombinant soluble proform of the enzyme purified from the periplasm. It consists of amino acid residues Tyr$^{89}$ to Gly$^{265}$ of mature human MT1-MMP (Calbiochem® catalog number 475935). The final concentration of each well is 0.5 nM instead of 0.2 nM as in MMP-2 assay. Data from representative compounds of the invention are provided below in Table 3.

TABLE 3

| Example | MMP1 IC50 (uM) | MMP2 IC50 (uM) | MMP3 IC50 (uM) | MMP7 IC50 (uM) | MMP8 IC50 (uM) | MMP9 IC50 (uM) | MMP12 IC50 (uM) | MMP13 IC50 (uM) | MMP14 IC50 (uM) |
| --- | --- | --- | --- | --- | --- | --- | --- | --- | --- |
| 1 | not tested | 1.75 | 2.845 | >100 | 0.0179 | 12 | 0.009 | 1.110 | 3.89 |
| 2 | 0.897 | 0.704 | 15.342 | >100 | <0.00510 | 0.439 | 0.026 | 4.189 | 7.99 |
| 3 | 39.2 | 35 | 99.710 | >100 | 0.804 | >100 | 0.268 | 46.952 | 50.2 |
| 4 | 56.8 | >100 | >100 | >100 | 5.22 | >100 | 3.365 | >100 | >100 |
| 5 | 4.55 | 4.652 | 13.165 | >100 | 0.054 | 7.59 | 0.071 | 4.808 | 14.870 |

MIA Injection PD Model in Rats

The assay as described in Swearingen et al., Osteoarthritis and Cartilage 18 (2010) 1159-1166, may be employed. MIA (Sigma, catalog #I2512, sodium salt) is prepared fresh on the day of use at 3 mg in 50 ul sterile 0.9% saline. 7-8-week-old male Lewis rats are anesthetized and injected intra-articularly with MIA into the right knee (to induce endogenous aggrecanase activity and the release of aggrecan fragments into the synovial fluid) and saline in the left (contralateral) knee on day 0. Aggrecanase inhibitor (3, 10 or 30 mg/kg) or vehicle [1% hydroxyethyl cellulose (HEC); 0.25% Tween 80; 0.05% antifoam] are dosed orally, twice a day starting from day 3. A single dose of compound is given on day 7, the animals are sacrificed 4 h later, and the knee joints are lavaged with 200 ul saline. The synovial lavage is assayed for aggrecanase-cleaved fragments of aggrecan using the NITEGE sandwich ELISA. The amount of aggrecan fragments present in the synovial lavage is determined based on a standard curve generated with aggrecanase-digested rat aggrecan. Statistical analysis is performed using Dunnett's test. Sandwich ELISA assay: For the NITEGE ELISA, the a-NITEGE monoclonal antibody is immobilized on white high binding ELISA plates (Nunc) overnight at 4 C. Following blocking, rat synovial fluid lavage samples are added to the plate and fragments with a C-terminal NITEGE sequence are captured. The captured fragments are detected using the HRP-conjugated a-HABR monoclonal antibody. The ELISA signal is measured using the Supersignal ELISA femto maximum sensitivity substrate (Pierce) and read on a Victor luminometer. The amount of aggrecan fragments present in the sample is determined based on a standard curve generated with aggrecanase-digested rat chondrosarcoma aggrecan (850 mg/ml stock diluted in antibody dilution buffer). Data is presented in Table 4.

TABLE 4

|  | Saline | Saline SEM | MIA | MIA SEM | % Inhibition | P Value |
|---|---|---|---|---|---|---|
| Vehicle | 4.00 | 0.62 | 27.02 | 4.29 |  |  |
| Example 1 10 MPK |  |  | 15.87 | 0.92 | 41.3 | 0.0052 |
| Example 1 30 MPK |  |  | 14.00 | 1.57 | 48.2 | 0.0011 |
| Example 1 100 MPK |  |  | 8.06 | 1.29 | 70.2 | <0.0001 |

Study of the Plasma Biomarker ARGN in Osteoarthritis Dogs

The objective of this study is to determine the plasma biomarker ARGN response in osteoarthritic (OA) dogs to a compound of the invention across a range of doses following daily oral administration for 21 days. Sixteen (16) adult laboratory Beagle dogs ≥8 years of age with radiographic evidence of OA in the hip joint(s) and 4 age matched control Beagle dogs without OA are enrolled in the study.

Blood samples for baseline plasma ARGN concentrations are collected from all dogs on 30, 28, and 26 days to prior to beginning dose administration. The 16 dogs with OA are block randomized by their average baseline plasma ARGN concentrations to 1 of 4 treatment groups: placebo, 0.1, 1, and 10 mg/kg of the Example 2 compound. The 4 age matched control dogs without OA all are assigned to the placebo treatment group. Beginning on Day 0, dogs receive once daily oral gavage administration of the Example 2 compound in a solution/suspension for 3 weeks according to their assigned treatment group. Blood samples for plasma ARGN and the Example 2 compound concentration determination are collected prior to the first dose administration and 3 times weekly for 4 additional weeks (Day 28). Additional blood samples for plasma ARGN and the Example 2 compound concentration determination are collected prior to and 1, 2, 6, 12, and 24 hours following the last dose administration (Day 20). Plasma ARGN concentrations are determined by immunoassay using a sandwich ELISA protocol and the Example 2 compound plasma concentration is determined using an LC-MS/MS method. Summary statistics of the plasma ARGN and Example 2 compound concentrations are calculated and a noncompartmental PK analysis of the Example 2 compound concentrations is conducted.

Plasma ARGN concentrations are inhibited in a dosage responsive manner with mean Day 21 inhibitions of 33.8%, 70.7%, and 80.3% following daily dosing with 0.1, 1, and 10 mg/kg of the Example 2 compound, respectively. The ARGN inhibition in normal and OA placebo treated dogs is comparably low, ranging from −1.30% to 13.4%. ARGN concentrations are not substantially different between normal and OA placebo dogs. The Example 2 compound plasma concentrations increase with dosage in a sub-proportional manner and steady-state trough concentrations are rapidly achieved. It is evident that increasing dosages and systemic exposure of the Example 2 compound results in increased inhibition of plasma ARGN concentrations. Therefore, the Example 2 compound inhibits its target aggrecanase in dogs with naturally occurring OA following once daily oral administration.

The invention is described by the following clauses.

1. A compound having the formula:

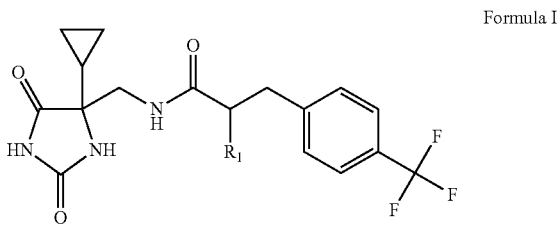

Formula I wherein $R_1$ is selected from methyl, ethyl, propyl, dimethyl, and cyclopropyl, or a pharmaceutically acceptable salt thereof.

2. The compound according to clause 1 having the formula:

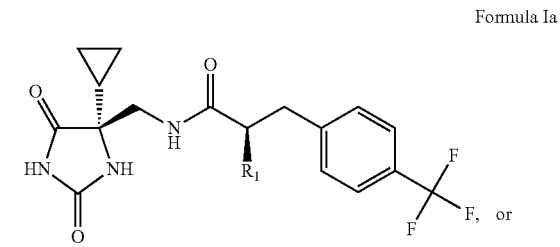

Formula Ia or

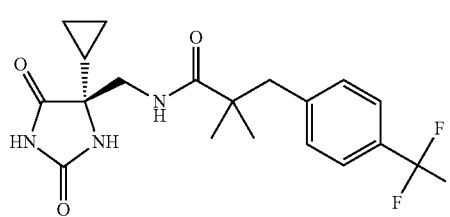

Formula Im or a pharmaceutically acceptable salt thereof.

3. The compound according to clause 1 having the formula:

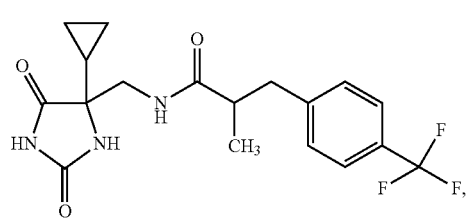

Formula Ib or a pharmaceutically acceptable salt thereof.

4. The compound according to clause 3 having the formula:

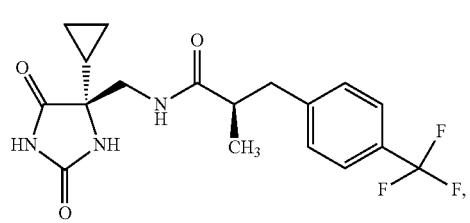

Formula Ic or a pharmaceutically acceptable salt thereof.

5. The compound according to clause 1 having the formula:

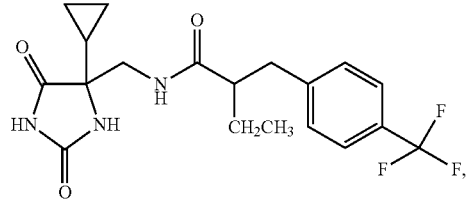

Formula Id or a pharmaceutically acceptable salt thereof.

6. The compound according to clause 5 having the formula:

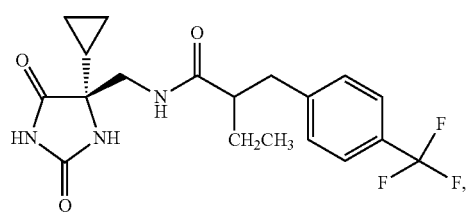

Formula Ie or a pharmaceutically acceptable salt thereof.

7. The compound according to clause 1 having the formula:

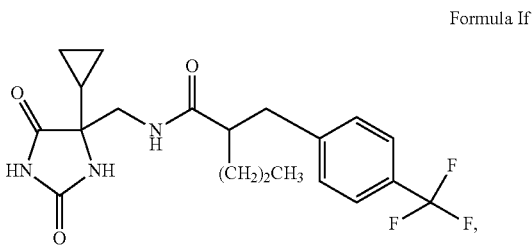

Formula If or a pharmaceutically acceptable salt thereof.

8. The compound according to clause 7 having the formula:

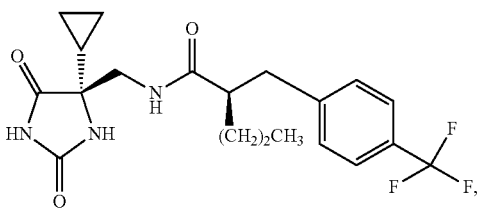

Formula Ig or a pharmaceutically acceptable salt thereof.

9. The compound according to clause 1 having the formula:

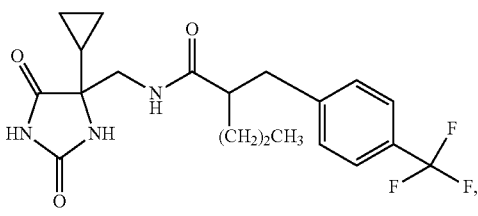

Formula Ih or a pharmaceutically acceptable salt thereof.

10. The compound according to clause 9 having the formula:

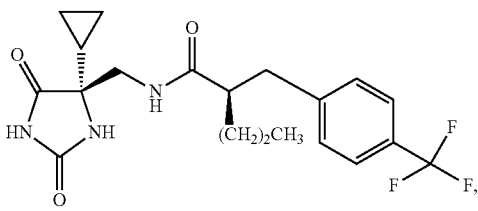

Formula Ii or a pharmaceutically acceptable salt thereof.

11. The compound according to clause 1 having the formula:

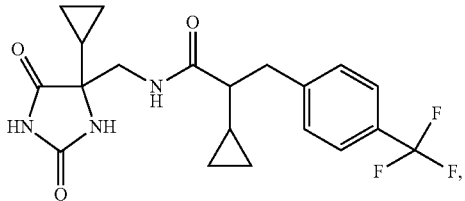

Formula Ij or a pharmaceutically acceptable salt thereof.

12. The compound according to clause 11 having the formula:

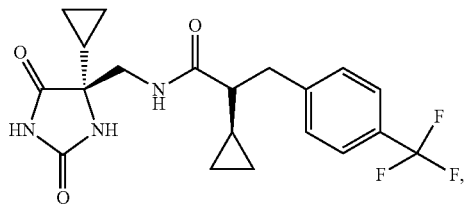

Formula Ik or a pharmaceutically acceptable salt thereof.

13. The compound according to clause 1 having the formula:

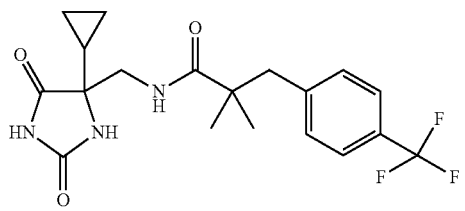

Formula Il or a pharmaceutically acceptable salt thereof.

14. The compound according to clause 13 having the formula:

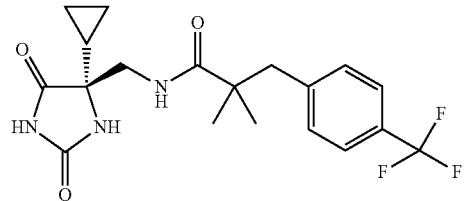

Formula Im or a pharmaceutically acceptable salt thereof.

15. A pharmaceutical composition comprising a compound according to any one of clauses 1 to 14, or a pharmaceutically acceptable salt thereof, and at least one of a pharmaceutically acceptable carrier, excipient, or diluent.

16. The pharmaceutical composition of clause 15, wherein said composition includes at least one additional active agent.

17. The pharmaceutical composition of clause 15 or 16, wherein said composition is a human pharmaceutical composition.

18. The pharmaceutical composition of clause 15 or 16, where said composition is a veterinary composition.

19. The pharmaceutical composition of any of clauses 15 to 18, wherein said pharmaceutical composition is adapted for oral administration.

20. The pharmaceutical composition of any of clauses 15 to 19, wherein said pharmaceutical composition is in the form of a tablet, capsule, solution, or suspension.

21. A method of treating arthritis in a patient in need thereof, said method comprising administering an effective amount of a compound according to any one of clauses 1 to 14, or a pharmaceutically acceptable salt thereof, to said patient.

22. The method of clause 21, wherein said patient is administered at least one additional active agent.

23. The method of clause 21 or 22, wherein said patient is a human.

24. The method of clause 21 or 22, wherein said patient is a dog.

25. The method of any of clauses 21 to 24, wherein said administration is oral administration.

26. The method of any of clauses 21 to 25, wherein said administration is carried out using said compound in a tablet, capsule, solution, or suspension.

27. A method of inhibiting cartilage erosion in a patient in need thereof, said method comprising administering an effective amount of a compound according to any one of clauses 1 to 14, or a pharmaceutically acceptable salt thereof, to said patient.

28. The method of clause 27, wherein said patient is administered at least one additional active agent.

29. The method of clause 27 or 28, wherein said patient is a human.

30. The method of clause 27 or 28, wherein said patient is a dog.

31. The method of any of clauses 27 to 30, wherein said administration is oral administration.

32. The method of any of clauses 27 to 31, wherein said administration is carried out using said compound in a tablet, capsule, solution, or suspension.

33. A compound according to any one of clauses 1 to 14, or a pharmaceutically acceptable salt thereof, for use in therapy.

34. A compound according to any one of clauses 1 to 14, or a pharmaceutically acceptable salt thereof, for use in the treatment of arthritis.

35. A compound according to any one of clauses 1 to 14, or a pharmaceutically acceptable salt thereof, for use in the inhibition of cartilage erosion.

36. The use of a compound according to any of clauses 1 to 14, or a pharmaceutically acceptable salt thereof, for the manufacture of a medicament.

37. The use of clause 36, wherein said medicament is for treating arthritis.

38. The use of clause 36 or 37, wherein said medicament is for inhibiting cartilage erosion.

39. The use of any of clauses 36 to 38, wherein said medicament is adapted for oral administration.

40. The use of any of clauses 36 to 39, wherein said medicament is in the form of a tablet, capsule, solution, or suspension.

The invention claimed is:

1. A compound having the formula:

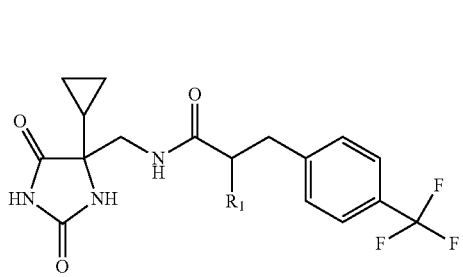

Formula I wherein $R_1$ is selected from methyl, ethyl, propyl, dimethyl, and cyclopropyl, or a pharmaceutically acceptable salt thereof.

2. The compound according to claim 1 having the formula:

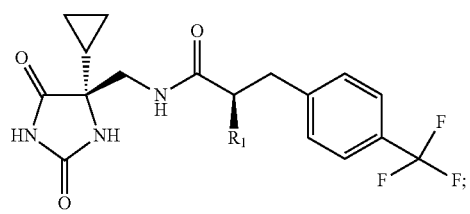

Formula Ia or a pharmaceutically acceptable salt thereof.

3. The compound according to claim 1 having the formula:

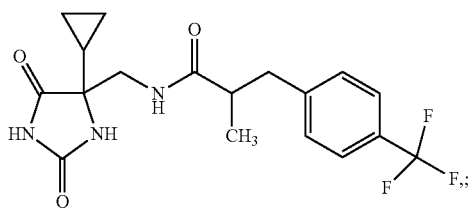

Formula Ib

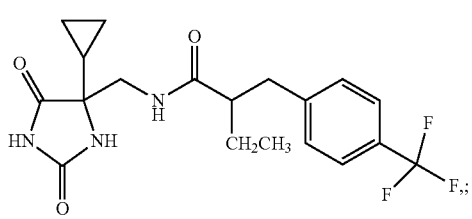

Formula Id

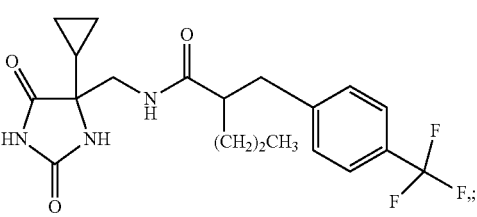

Formula If

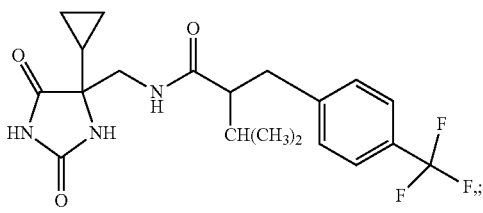

Formula Ih

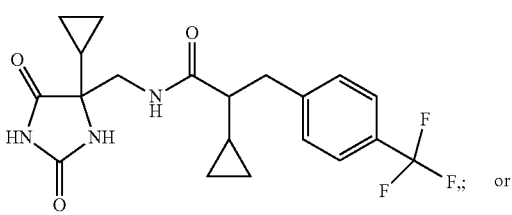

Formula Ij

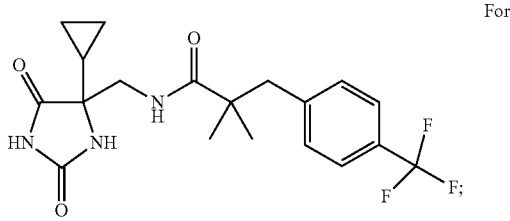

Formula Il or a pharmaceutically acceptable salt thereof.

4. The compound according to claim 3 having the formula:

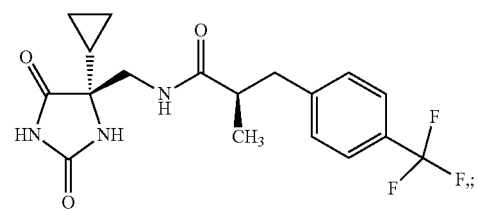

Formula Ic

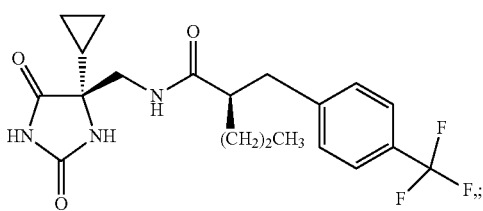

Formula Ig

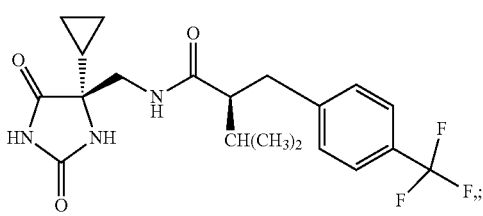

Formula Ii

-continued

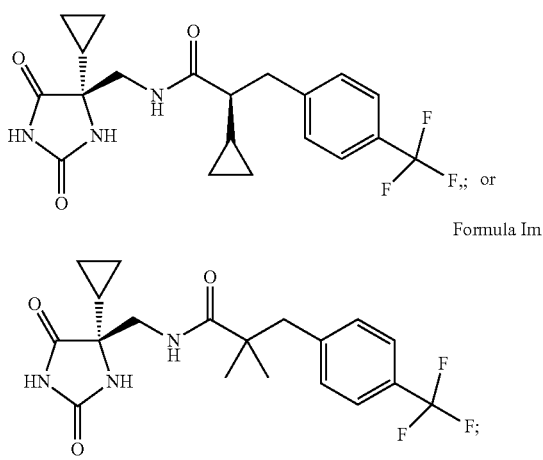

Formula Ik

Formula Im or a pharmaceutically acceptable salt thereof.

5. The compound according to claim 1 having the formula:

Formula Ib

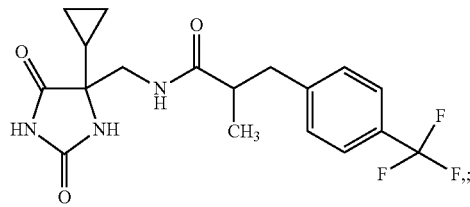

or a pharmaceutically acceptable salt thereof.

6. A pharmaceutical composition comprising a compound according to claim 1, or a pharmaceutically acceptable salt thereof, and at least one of a pharmaceutically acceptable carrier, excipient, or diluent.

7. The pharmaceutical composition of claim 6, wherein said pharmaceutical composition is adapted for oral administration.

8. A method of treating arthritis in a patient in need thereof, said method comprising administering an effective amount of a compound according to claim 1, or a pharmaceutically acceptable salt thereof, to said patient.

9. The method of claim 8, wherein said patient is administered at least one additional active agent.

10. The method of claim 8, wherein said patient is a human.

11. The method of claim 8, wherein said patient is a dog.

12. The method of claim 8, wherein said administration is oral administration.

13. A method of inhibiting cartilage erosion in a patient in need thereof, said method comprising administering an effective amount of a compound according to claim 1, or a pharmaceutically acceptable salt thereof, to said patient.

14. The method of claim 13, wherein said patient is administered at least one additional active agent.

15. The method of claim 13, wherein said patient is a human.

16. The method of claim 13, wherein said patient is a dog.

17. The method of claim 13, wherein said administration is oral administration.

* * * * *